United States Patent [19]

Bjørn

[11] Patent Number: 5,733,271
[45] Date of Patent: Mar. 31, 1998

[54] VALVE DEVICE FOR ABSORPTION OF THE GAS COMPONENTS

[76] Inventor: Per Ole Bjørn, P.O. Box 2132, N-9002 Tromsø, Norway

[21] Appl. No.: 581,613

[22] PCT Filed: Jul. 15, 1994

[86] PCT No.: PCT/NO94/00127

§ 371 Date: Feb. 21, 1996

§ 102(e) Date: Feb. 21, 1996

[87] PCT Pub. No.: WO95/03015

PCT Pub. Date: Feb. 2, 1995

[30] Foreign Application Priority Data

Jul. 19, 1993 [NO] Norway ............................ 932605
Apr. 25, 1994 [NO] Norway ............................ 941499

[51] Int. Cl.⁶ ............................................ A61F 5/44
[52] U.S. Cl. ............... 604/333; 55/385.4; 55/482; 55/486; 604/338
[58] Field of Search ........................ 604/332, 333, 604/338; 55/355, 385.4, 482, 486; 137/251.1, 386, 388

[56] References Cited

U.S. PATENT DOCUMENTS

| | | |
|---|---|---|
| 4,449,970 | 5/1984 | Bevan et al. |
| 4,938,749 | 7/1990 | Jensen. |

FOREIGN PATENT DOCUMENTS

| | | | |
|---|---|---|---|
| 147293 | 7/1983 | Denmark. | |
| 235 928 | 9/1987 | European Pat. Off.. | |
| 30 36 009 | 4/1981 | Germany. | |
| 139029 | 7/1977 | Norway. | |
| 154904 | 10/1982 | Norway. | |
| 161293 | 12/1984 | Norway. | |
| 454239 | 9/1983 | Sweden. | |
| 1363644 | 8/1974 | United Kingdom | 604/333 |
| 2094153 | 9/1982 | United Kingdom | 604/333 |

*Primary Examiner*—Robert A. Clarke
*Attorney, Agent, or Firm*—Bell Seltzer Intellectual Property Law Group of Alston & Bird LLP

[57] ABSTRACT

A valve device having a filter with at least a lower and upper compartment. The lower compartment is in fluid communication with a collection bag via apertures. The lower compartment is defined by a first division plate and a bottom wall. This lower compartment is filled with an odor absorbing substrate. One embodiment includes two lower compartments wherein the gas entering the lower compartment from the collection bag through the apertures, circulates along the length of the compartment, around the lower division plate, and along the length of the compartment toward the opening.

8 Claims, 4 Drawing Sheets

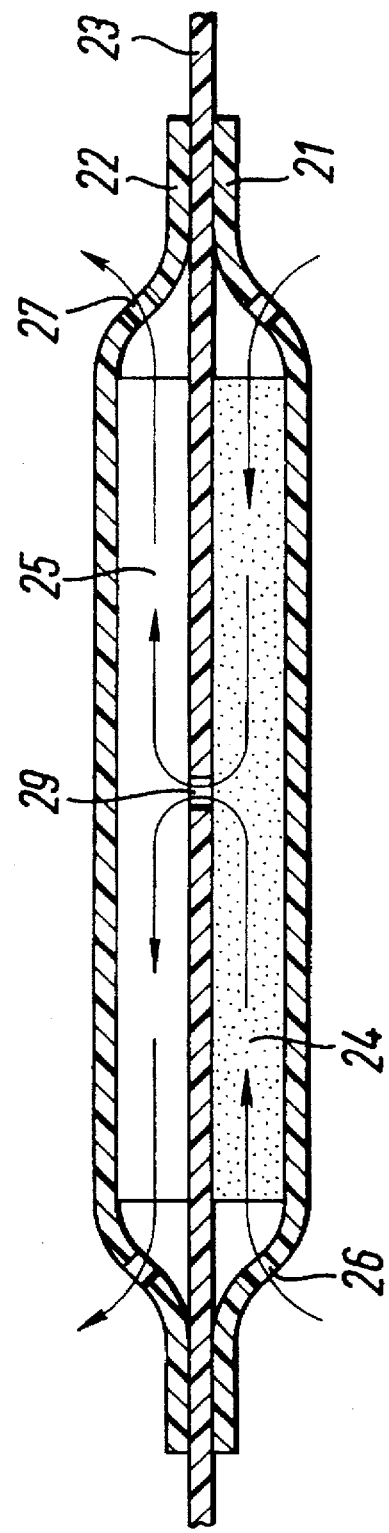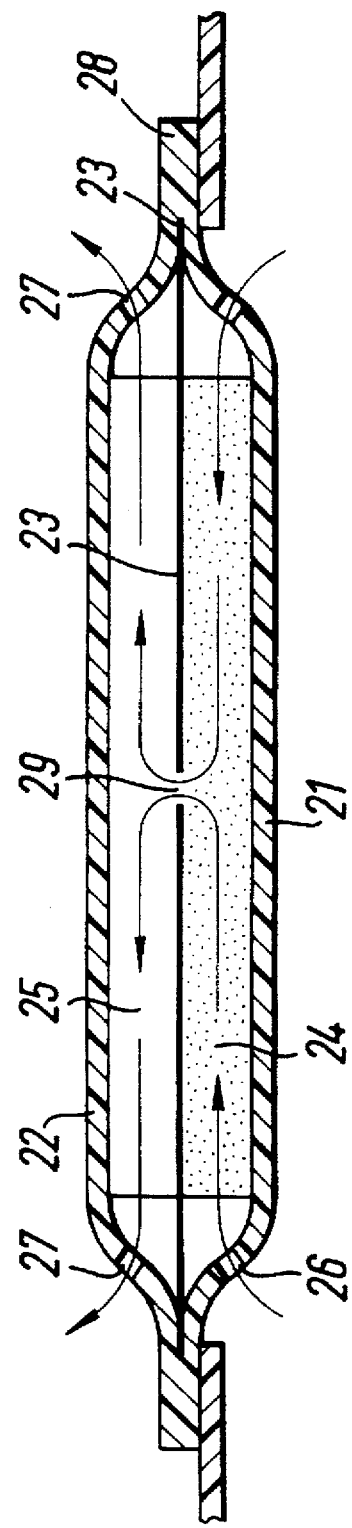

VALVE DEVICE FOR ABSORPTION OF THE GAS COMPONENTS

FIELD OF THE INVENTION

This invention concerns a valve device or filter house which can be used, for example, in stoma bags, especially ileostomy bags, which in one embodiment have an extended gas transport path, and which are self-closing when the moisture in the filter exceeds a certain limit.

BACKGROUND OF THE INVENTION

Surgical procedures such as colostomy, ileostomy and urostomy, where a permanent opening is created between the body's internal cavity and the environment, apart from the natural orifices, makes it necessary for the patient to permanently wear a bag for the collection of bodily fluid, possibly faeces and faecal particles. This is necessary because the body's natural orifices have shut-off musculature, such as sphincter musculature, which is subject to voluntary control, while a surgical stoma will directly discharge bowel contents/urine without the person having very much control over the process. The composition of the discharges in the case of bowel stomata will be dependent on at which point in the intestine the operation was performed, so that, e.g., in the case of a colostomy the discharge will be of a thicker, almost normal consistency, since a part of the water reabsorption capacity will be intact, while in the case of ileostomy the discharge will include particles of different sizes in a thin liquid. In both cases intestinal gas, which is formed continuously in amounts from 50–1200 ml per day, measured as the amount which passes through the anus, will be passed out into the bag together with the bowel contents. Thus in the case of stomata, a considerable amount of gas could be passed out into the bag every day.

Intestinal gas or flatus (intestinal gas which emerges through the anus) contains nitrogen, carbon dioxide, hydrogen, methane and trace elements in varying amounts. Compositions have been measured (Kodama and Miura, J. Japan. Soc. Nutr. 2:149–152, 1949) such as 13–34% $CO_2$, 19–26% $CH_4$, 20–27% $H_2$, 17–48% $N_2$ and less than 1% of indole, skatol, volatile amines and hydrogen sulphide. The latter constitute the malodorous substances in flatus and it is claimed that $H_2S$ can be detected by the sense of smell in as low a concentration as one part $H_2S$ in 100 million (0.01 dpm). Thus a bad smell can constitute a substantial disadvantage when wearing a stoma bag.

Since substantial amounts of malodorous intestinal gas can thus be produced and passed out into a stoma bag, this bag would rapidly become inflated if it was not provided with an outlet valve, and due to the smell this valve also requires a filter which removes odour by absorption, as it contains a deodorant material. A filter of this kind has to provide a sufficient contact area between the odour-absorbing material and the gas for adequate absorption of the odour, and the filter must be able to prevent or reduce the formation of moisture in the filter because a moist filter does not absorb gas. In the base of ileostomies, the build-up of moisture in the filter constitutes a particularly serious problem compared with colostomy, since the discharge is mainly liquid. Thus during the night it is difficult to avoid exposing the filter to liquid.

Attempts have been made to solve these problems in a number of patents, such as NO-PS 139029, 154904, 161293, SE-PS 454239 and DE-PS 3036009.

The prior art comprises the use of active carbon in the filter device with various designs for extending the gas flow path in the filter, such as the case in which the valve device constitutes a plug where the gas circulates in winding channels formed in the actual filter or where the valve device has standing walls which force the gas to circulate on a plane parallel to the valve device's outer top, which is parallel to the bag's surface and thereby increases the gas flow path approximately five times (NO-PS 139029), or where the filter is oblong with an inlet opening for gas and an outlet opening near each end (NO-PS 161293) or where the filter is composed of a gas channel round the periphery of the related stoma bag (NO-PS 154904). The most common filter available on the market, which is based on SE-PS 454239, permits the gas to flow through the thickness of the filter and includes no other modification for extending the gas flow path through the filter than that the gas enters the centre of the filter, through an opening which is substantially smaller than the radius of the filter and smaller than the gas outlet opening from the filter, the transport path thus passing obliquely through the filter and thereby being extended. A filter of this kind can, e.g., be 20 mm in diameter, with a thickness of 2 mm and the transport path will be approximately 10 mm.

Further factors which reduce the capacity of the filter are the production of channels in the filter mass, during which process the active carbon is removed from the walls or show lacking cohesion in the middle of the filter mass and falls apart. The gas will follow the path of least resistance and will not be forced to circulate the whole filter mass, and the absorption capacity is reduced.

This problem is tried solved in DK-B2-147 293, in which the diffusion path for the gases is no longer than from the periphery of the filter to the centre. However, the filter material consists of a special cotton matrix in which a great amount of fine granulated active carbon is embedded, enveloped by a gas-proof plastic dispersion. This gives a good cohesion in the finely granulated carbon, and the plastic dispersion penetrates the filter mass on several places and anchor the two layers to each other. Consequently the filter mass does not loosen from the walls, and the particles will not fall apart. The gas is thereby forced through the whole of the gas-absorbing mass.

A common problem for all filters included in the prior art is, however, as mentioned above, that when the filter becomes moist the filter mass's odour absorption is reduced or ceases, thus allowing malodorous intestinal gas to be released into the environment. This is a serious problem for patients who are obliged to wear a stoma bag permanently.

Attempts have been made to solve this problem in the prior art by placing a barrier layer of gas-permeable but moisture-impermeable material on the gas inlet side of the filter (NO-PS 161293, NO-PS 139029, DE-PS 3036009). However, this or these hydrophobic layers can cause a blockage problem, the passage of gas in the moisture-inhibiting layer being reduced or obstructed when particles and more solid contents of the bowel discharge cover the filter surface and reduce the through-flow of gas. Especially in connection with ileostomi the content of solid particles is considerable.

EP-A-0 235 928 comprises a deodorizing filter for ostomy equipment, where a filter body of a thickness of 0,25–3,0 mm is encased in a housing of a flexible plastic sheet material. The inlet opening and the outlet opening of the filter are located at the maximum distance from each other, at least 10 mm, preferably 30 mm. In preferred embodiments of the filter, particularly suitable for ileostomi, the filter housing is provided on the side thereof facing the source of the intestinal gas with a covering sheet with openings for the passage of incoming intestinal gas and/or with a layer of liquid-absorbing material.

SUMMARY OF THE INVENTION

In this filter a liquid-absorbing material is located upstream of the filter body, in such a way that the absorbent material does not cover the inlet opening for intestinal gas to be deodorized. Thus this invention cannot prevent liquid from entering the filter body when the absorbing capacity of the material is exhausted, which would prevent the deodorizing action of the filter body and produce unpleasant odour.

Thus it is the object of the present invention to provide pouch with a valve device with filter which gives a larger effective exposure surface between the gas and the gas component absorbing material than filters which are included in the prior art, is especially suitable for, for example ileostomies, in that the gas flow is stopped by the channel being closed when the filter becomes moist and inflation of the bag signals that the filter/bag must be changed.

BRIEF DESCRIPTION OF THE DRAWINGS

FIG. 4a is a cross-sectional view of a valve device according to a second embodiment of the present invention; and FIG. 4b is another cross-sectional view thereof.

Figure 1A:
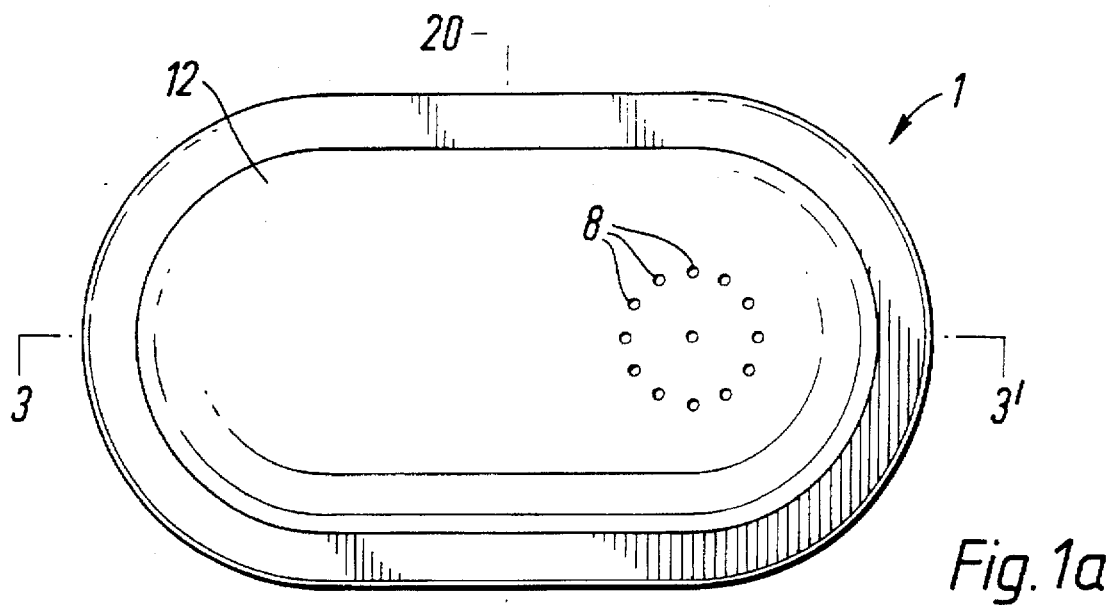
FIG. 1a is top plan view of valve device according to the present invention.

The present invention comprises a valve device 1 which can be attached to a valve opening 2 in, e.g., a stoma bag by means of a known reversible, rapid lock technique or can be permanently welded to the bag or be an integrated part of the bag in that the wall of the bag serves as one of the valve walls. The valve device is round or oblong, with or without rounded ends viewed in a plane parallel to the wall 14 of the bag, and consists of a number of compartments, for example three compartments, 5, 6 and 7, defined by the device's bottom 9, lower division plate 10, upper division plate 11 and top 12, all with openings 4, 15, 16 and 8 for gas through-flow, where the two lowest compartments 5 and 6 are filled with an odour-absorbing means, and the upper compartment is filled with a means which expands when it becomes moist. In a second design the valve device consists of two compartments 24, 25 with inlet openings 26 and outlet openings 27 localized in the periphery of the valve and opening 29 in the centre of the intermediate wall 23. The lower compartment 24, the gas absorption compartment, is filled with gas-absorbing means and the upper compartment, the expansion compartment, is filled with a means which expands when moist. This means can be in powder form or in the form of a body.

Figure 1B:
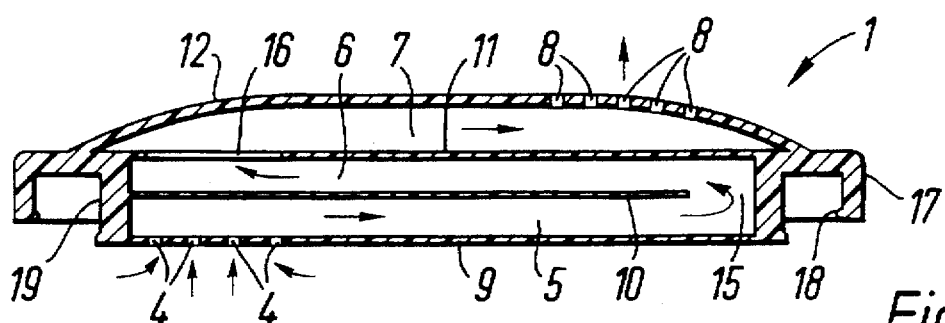
FIG. 1b is a cross-sectional view taken along lines 3—3' of FIG. 1.
Figure 1C:
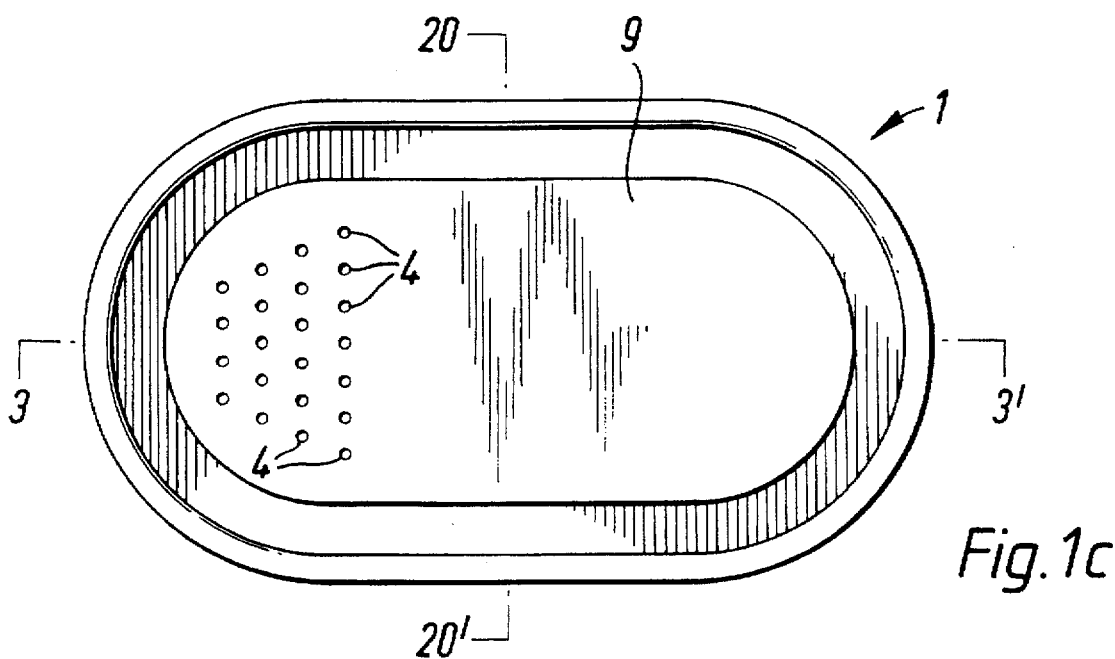
FIG. 1c is a bottom plan view thereof.
Figure 2A:
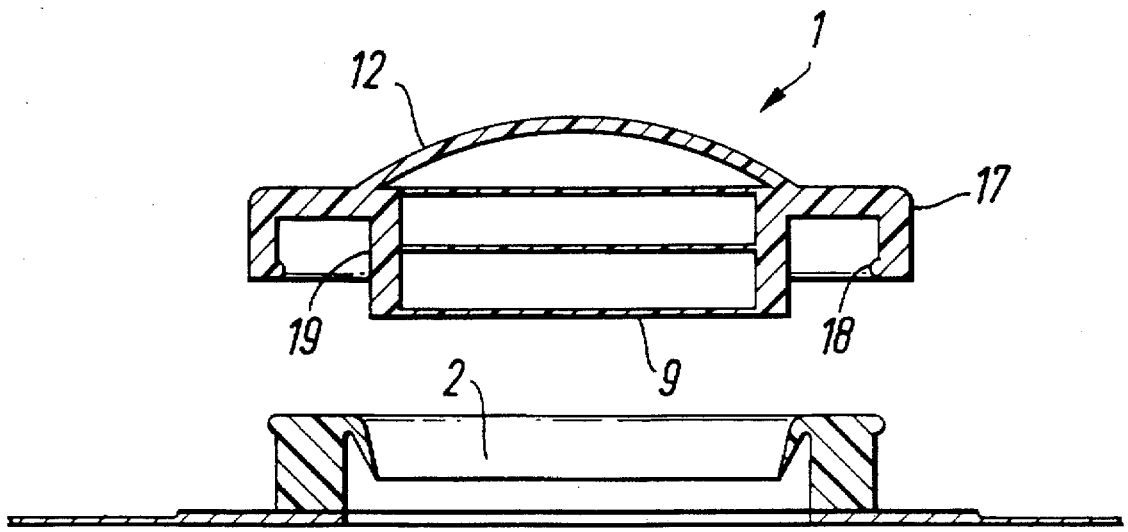
FIG. 2a–2b are cross-sectional views taken along line 20—20' of FIG. 1.
Figure 2B:
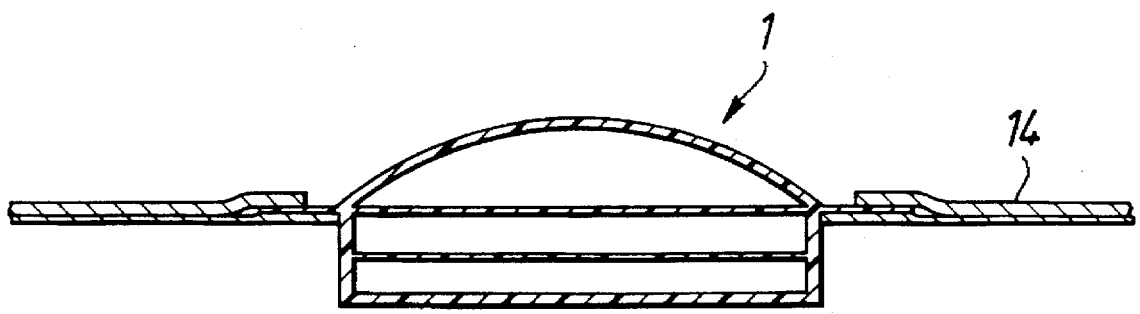
Figure 3A:
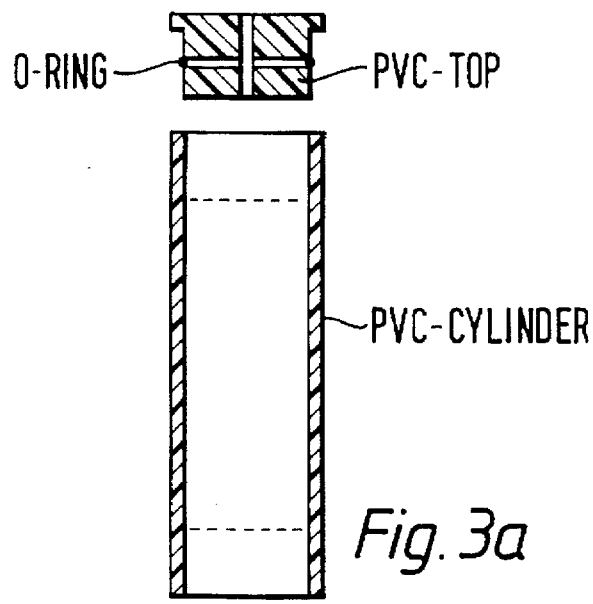
FIGS. 3a to 3c are cross-sectional views of a test apparatus.
Figure 3B:
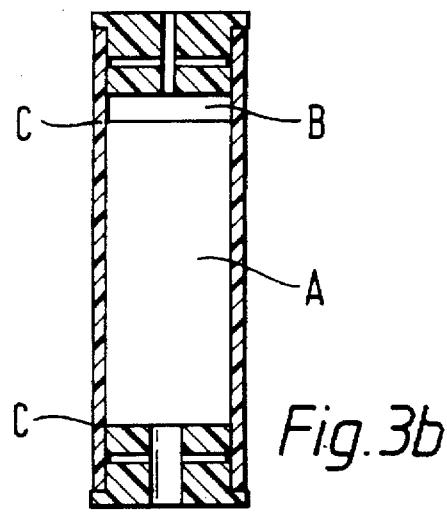

The different versions of the invention will now be described in detail with reference to the figures, where FIG. 1 illustrates (a) the valve device viewed from the outlet side, (b) a cross section along the valve device's longest axis (line 3—3' in FIG. 1a) and (c) the valve device viewed from the gas inlet side;

FIG. 2 illustrates a section of the valve device through line 20—20' in FIG. 1 and demonstrates the possibilities for attaching the device to a stoma bag, either a reversible rapid lock (a) or permanently welded into the stoma bag (b);

FIGS. 3a, b, and c illustrates a test apparatus for testing an expanding substance's ability to stop the through-flow of gas under the influence of moisture. A is active carbon, B is the expanding substance during testing and C is a partition of gas. Panel b shows the filter cylinder with attached balloon, filled with air and water, and FIGS. 4a and b illustrate a second design of the invention with two compartments and granulated active carbon-impregnated foam as gas absorption means.

Figure 3C:
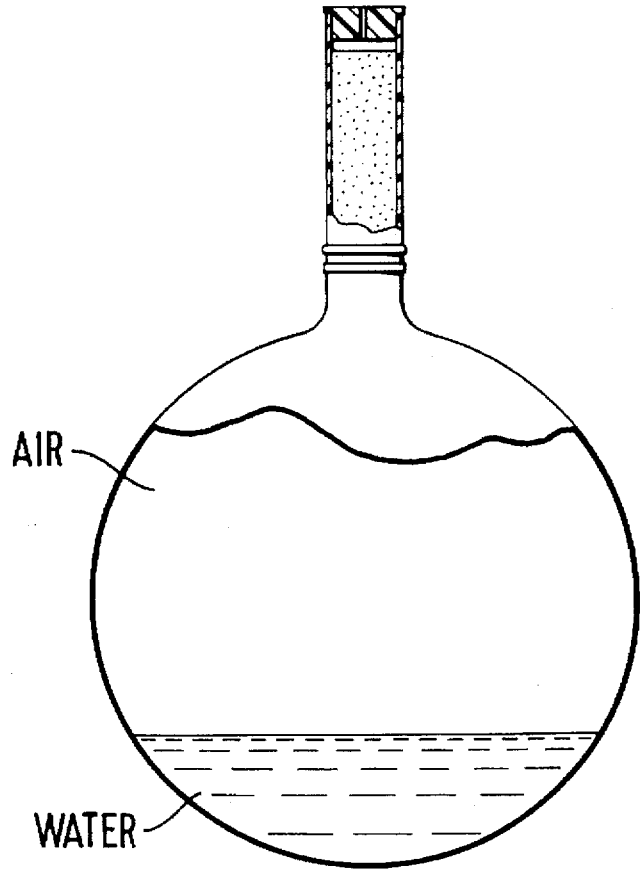

FIG. 1 illustrates a version of the valve device according to the present invention, consisting of three adjacent compartments 5, 6 and 7, where the gas enters the valve device through a perforated opening 4 on the end of the device in the bottom 9, circulates from compartment 5 to compartment 6 through an opening 15 in the lower division plate 10 at the valve device's opposite end, circulates back and into compartment 7 through an opening 16, located in the upper division plate 11 at the first end, immediately above the gas inlet 4, and the gas flows on into the compartment 7 towards the valve device's other end and leaves the valve device through gas outlet 8, located near the other end. In a round arrangement of the valve device the openings are located with mutual maximum distance between each opening. A flange 17 round the valve device is designed with a turned down outer part, provided with a projection 18 pointing towards the valve device and thus coming into engagement with a projection directed from the valve device aperture on a collar round the stoma bag opening (FIG. 3a). This attaching mechanism, which is reversible, can be found, e.g., on stoma bags produced by ConvaTec and is known in the prior art. In another version the valve device is equipped with a single flange around the periphery which is used when the valve device is permanently welded to the bag by means of the prior art (FIG. 3c).

The valve device is made of a suitable material which does not react chemically with the filter contents. In a preferred embodiment the device is made of a suitable plastic material.

The lower division plate 10 which separates compartments 5 and 6 is parallel to the bottom 9 and upper division plate 11 and located in such a manner that the heights in compartments 5 and 6 are the same. Opening 15 is located at the other end, opposite the gas inlet 4. Opening 16 is located at the first end opposite opening 15 and this gives a substantially extended diffusion path while at the same time the gas comes into contact with the odour-absorbing means over the entire width of the valve device. This constitutes a profoundly enlarged contact surface compensating for possible creation of channels in the odour-absorbing mass, with a considerably larger surface than that to which the gases are exposed in, e.g., NO-PS 139029,where the gas circulates in channels formed in the odour-absorbing medium or in channels formed in perpendicular walls in the filter device. The odour-absorbing means can comprise active carbon, another deodorant means or a means which itself has a smell or a mixture of these means.

In the upper compartment 7, defined by the upper division plate 11 and the top 12, there is filled a medium which is porous and gas permeable when dry, but which swells under the influence of moisture and closes the gas outlet. Suitable means can include powderous plaster, sand or a a powder mixture of plaster and sand in suitable proportions in the region of 30:70 to 70:30 (plaster:sand), preferably 50:50, dried and compressed synthetic sponge material or superabsorbent such as sold commercially as SUPERABSORBENS, LIC™, or any porous medium which swells when damp. Since compartment 7 is limited by relatively rigid walls, 11, 12, the swelling will cause the gas flow to stop and no gas will be released from the bag even though the swelling stops the gas outlet through the porous medium without this being enveloped by rigid walls. The bag will then swell and this is a signal that the filter has to be changed. The valve device 1 with two filter layers and moisture-swelling mass is manufactured as a unit, replaced by a new one when the gas outlet is clogged, and discarded.

FIGS. 4a and b illustrate a second design of the valve device according to the invention. This design has a division plate 23 and is separated in a lower 24 and an upper 25 compartment. The outer walls of the valve device have a number of inlet openings 26 for gas in the wall 21 towards the interior of the stomi bag and a number of outlet openings 27 for gas in the wall 22 facing the ambience, where both sets of openings 26, 27 are located in the periphery of the valve device and such that the set of openings 26 leads the gas into the lower compartment 24 and the set of openings 27 leads the gas out of the upper compartment 25. The division plate 23 separating the two compartments 24 and 25 have an opening in the centre.

The walls 21, 22 and the division plate 23 are produced in any suitable material, for example plastic material which is gas-proof and moisture-proof. In the periphery of the valve device the upper wall 22, the lower wall 24 and the division plate 23 are melted together to form a flange surrounding the whole valve device (FIG. 4b). This flange can be heat sealed in a suitable opening in the stoma bag. In a second design (FIG. 4a) the valve device is produced as an integrated part of the stoma bag such that the outer wall of the bag constitutes the division plate 23 and the valve device walls 21 and 22 are attached on the inside and outside, respectively, of the bag by a gas-proof sealing. In both designs the valve design is permanently attached to the stoma bag.

The lower compartment 24 is filled with a gas-absorbing substrate in a form which prevents creation of channels, for example granulated active carbon impregated in a synthetic foam. In this foam impregnated with granulated active carbon, the carbon is attached so firmly to the pore walls that the particles do not loosen. Hence the gas will be exposed to the absorption capacity ofthe whole filter mass and the previously mentioned creation of channels is avoided.

The upper compartment 25 is filled with a material which swells or expands when moist and closes the gas outlet. Suitable means are mentioned previously.

The odorous, moist intestinal gas enters the valve device through the openings 26, passes through the odour-absorbing material which will not be canalized in the lower compartment 24, through openings 29, into the upper compartment 25 and leaves through the openings 27. Deposition of moisture in the filter material, which in the lower compartment will lead to a reduction of the odour absorption, according to the present invention will lead to swelling of the substrate in the upper compartment and closure of the gas outlet. Exposure of moisture in the form af a direct contact between the valve device and liquid in the stoma bag will produce the same effect. The stoma bag will inflate as a signal to change the valve device/bag. Even through the gas pressure in the bag increases with t accumulation of gas the closed filter remains gas-proof.

The present design of the valve device is not limited to any specific shape, a the number of division plates in the valve device can be increased such that there are several separated layers with gas-absorbing substrate, while at least one upper compartment always will contain a moisture expanding substrate.

In the following the invention will be further described and illustrated by examples.

EXAMPLE 1

A Test Apparatus for Testing the Filter Mass in the Valve Device

The test apparatus is illustrated in FIGS. 3a, b, and c and consists of a plastic cylinder, corked at both ends by perforated corks, where the downstream hole has a smaller diameter than the upstream hole. The cylinder is filled with, e.g., active carbon A, and the expanding substance B, during testing. Between the two layers there is a partition of gas C. To this filter cylinder there is fitted a bag of elastic, airtight material such as a balloon, which is filled approximately ¼ full of water and ¾ full of gas or air. When the test apparatus is put into operation, supported in such a manner that the filter cylinder is vertical and points upwards, the air/gas will leak out through the filter cylinder, the balloon will collapse and the filter cylinder will come into contact with water. The moisture will be drawn up through the filter and reach the test substance B.

By compressing the balloon it can be checked whether the filter cylinder has become blocked. This test apparatus simulates the situation in which a valve device according to the present invention is inserted in a stoma bag.

EXAMPLE 2

The Testing of Different Materials Which Expand Under the Influence of Moisture

The filter cylinder was filled with active carbon as test substance A and as test substance B there was used 1) a mixture of plaster and sand (50:50, plaster/sand), 2) dried synthetic sponge material, and 3) Superabsorbens, LIC™. The balloon was filled with air and water as described in example 1.

In all three cases the through-flow of air was stopped when the moisture reached the test substance B in the filter cylinder.

In all three cases the balloon was thereafter disconnected and the impermeability of the filter cylinder to the through-flow of gas was tested with air under a pressure of 6 bar. The filter cylinder did not allow air to pass through in any of the three cases.

EXAMPLE 3

Testing of the Second Valve Device Design According to the Invention with Ileostomi Bag The example shows a testing of ileostomi bags with the second design of the valve device according to the invention, in which the lower compartment 24 is filled with a synthetic foam impregnated with granulated active carbon, and the upper compartment 25 is filled with Superabsorbens, LIC™. The test continues over six days, and in the beginning of the period intake of food and liquid which is known to produce air in the gastrointestinal tract was emphasized. This intake is specified by time of the meal and the type of food consumed. No specific indication of time of meal and type of food means that normal meal rythm, comprising three bread meals and one dinner a day, was followed.

Day 1

5 p.m. A meal comprising salmon, shrimps, beer and champagne was consumed.

6 p.m. Bag 1 was attached.

9–11 p.m. Big meat supper with wine, beer and brandy.

1.30 a.m. Went to bed. The filter functioned all the time adequately without creation of odour.

Day 2

6.30 a.m. Awakening. The filter iss closed and the bag is slightly inflated by gas. The typical balloon shape which is common to ileostomic bags without valve device was not observed. Bag 1 was used all through the day.

8–9 p.m. Fish dinner with a lot of beer. Continued to use bag 1 in order to test whether an increased gas pressure in the stomic bag should open up the valve device. No reopening nor any smell was observed.

1.30 a.m. Bag 1, which was used for 31,5 hours, was disconnected. Bag 2 was connected.

Day 3

7 a.m. Awakening. The bag was slightly inflated, but the valve device was open. No odour was observed.

3 p.m. The valve device was completely closed.

23.30 p.m. The valve device was still closed. No odour was observed, and the bag worked like a common ileostomic bag without the valve device. Bag 2 was disconnected. Bag 2 was used for 34 hours. Bag 3 was connected.

Day 4

The valve device in bag 3 was closed during the night. Even though the bag showed no typical balloon-shape, which would have been the case of ileostomic bags without valve device, no odour or leak from the valve device was observed. Bag 3 was used all through the day and the following night.

Day 5

9 a.m. Bag 3 was disconnected after 33,5 hours' use. No balloon-shape, no leak, no odour was observed. Bag 4 was connected. The filter in this bag remained open and functioned all through the day. No smell was observed.

6 p.m. The valve device closed. The same bag was used all through the night.

Day 6

7 a.m. Awakening. No odour was observed, nor any leak, but the bag was now shaped like a balloon. Bag 4 was disconnected after 22 hours of use.

General Conclusion

The valve device according to the invention was tested in one subject during a period of 6 days, comprising a common Norwegian regime of meals in addition to some larger intake of air producing food at abnormal times of the day. The valve device worked adequately in this period, and if the bag is changed twice during 24 hours, all problems with air in the bag will be eliminated. It is especially promising that if a new bag with a valve device according to the invention is connected just before going to bed, it will last all through the night. This is a period when ileostomic bags will normally be exposed to the liquid content of the bag. Generally the valve device seems to be open longer in the day time when the subject is in a upright position, because the filter mass in this position will not easily be in contact with the liquid in the bag. When the valve device was taken apart, it was observed that only about 25% of the Superabsorbens was moist when the valve device was closed.

I claim:

1. A valve device useable with a collection bag comprising:
   a lower compartment defined by a gas and liquid impermeable bottom wall having at least one aperture arranged to fluidly communicate with a collection bag and a gas liquid impermeable first division plate;
   an odor-absorbing substrate positioned within said lower compartment;
   an upper compartment in fluid communication with said lower compartment and being defined on one side by a gas and liquid impermeable top wall having at least one aperture in communication with an external environment of the valve device in use; and
   an expandable substrate positioned within said upper compartment, said substrate being arranged within said upper compartment so that upon contact with moisture from said first compartment, said substrate expands to close said apertures in fluid communication with the external environment wherein gases from the collection bag are vented through the odor absorbing lower compartment, through the upper compartment and exit through said at least one aperture of the top wall but liquid is prevented from exiting the valve device.

2. A valve device according to claim 1 comprising a second division plate and an intermediate compartment defined by said first and second division plates and odor absorbing material positioned within said intermediate compartment, wherein said first division plate comprises an aperture such that said lower and intermediate compartments are in fluid communication and said second division plate comprises at least one aperture such that said intermediate and upper compartments are in fluid communication.

3. A valve device according to claim 1 wherein the odor absorbing substrate is a pore-forming matrix including adhesively attached active carbon and said gas and liquid impermeable upper and bottom walls are plastic.

4. A valve device according to claim 1 wherein said expandable substrate comprises at least plastic or sand.

5. A valve device according to claim 1 wherein said expandable substrate is a dried sponge of synthetic material.

6. A valve device according to claim 1 wherein said expandable substrate is a superabsorbent material.

7. A valve device according to claim 1 wherein said odor-absorbing substrate is a plastic impregnated with granulated active carbon.

8. A valve device in combination with a collection bag comprising a valve body having a lower compartment defined by a gas and liquid impermeable bottom wall having at least one aperture arranged to fluidly communicate with a collection bag and a gas liquid impermeable first division plate, an odor-absorbing substrate positioned within said lower compartment, an upper compartment in fluid communication with said lower compartment and being defined on one side by a gas and liquid impermeable top wall having at least one aperture in communication with an external environment of the valve device in use, an expandable substrate positioned within said upper compartment, said substrate being arranged within said upper compartment so that upon contact with moisture from said first compartment, said substrate expands to close said apertures in fluid communication with the external environment wherein gases from the collection bag are vented through the odor absorbing lower compartment, through the upper compartment and exit through the apertures of the top wall but liquid is prevented from exiting the apertures of the top wall, and a collection bag for intake and storage of waste products, said bag having gas and liquid impermeable walls wherein said valve device sealingly mates with said collection bag.

* * * * *